(12) United States Patent
Kreisler et al.

(10) Patent No.: US 12,082,957 B2
(45) Date of Patent: Sep. 10, 2024

(54) PHOTON-COUNTING X-RAY DETECTOR AND METHOD FOR OPERATING A PHOTON-COUNTING X-RAY DETECTOR

(71) Applicant: Siemens Healthcare GmbH, Erlangen (DE)

(72) Inventors: Bjoern Kreisler, Hausen (DE); Edgar Goederer, Forchheim (DE); Martin Hupfer, Erlangen (DE); Martin Petersilka, Adelsdorf (DE)

(73) Assignee: Siemens Healthineers AG, Forchheim (DE)

( * ) Notice: Subject to any disclaimer, the term of this patent is extended or adjusted under 35 U.S.C. 154(b) by 779 days.

(21) Appl. No.: 17/116,102

(22) Filed: Dec. 9, 2020

(65) Prior Publication Data
US 2021/0186440 A1     Jun. 24, 2021

(30) Foreign Application Priority Data
Dec. 18, 2019    (EP) .................................... 19217562

(51) Int. Cl.
*A61B 6/42*        (2024.01)
*A61B 6/03*        (2006.01)
(Continued)

(52) U.S. Cl.
CPC ............ *A61B 6/4241* (2013.01); *A61B 6/032* (2013.01); *A61B 6/4233* (2013.01); *G01T 1/17* (2013.01); *G01T 1/247* (2013.01)

(58) Field of Classification Search
CPC ..... A61B 6/4241; A61B 6/032; A61B 6/4233; G01T 1/17; G01T 1/247; G01T 1/161
See application file for complete search history.

(56) References Cited

U.S. PATENT DOCUMENTS

| 8,440,957 B2 | 5/2013 | Dierickx |
| 8,772,730 B2 | 7/2014 | Han et al. |

(Continued)

FOREIGN PATENT DOCUMENTS

| CN | 103858022 A | 6/2014 |
| CN | 106061393 A | 10/2016 |

(Continued)

OTHER PUBLICATIONS

Hsieh, S., "Coincidence counters for charge sharing compensation in spectroscopic photon counting detectors", IEEE Transactions on Medical Imaging, doi: 10.1109/TMI.2019.2933986.

(Continued)

*Primary Examiner* — Christine S. Kim
(74) *Attorney, Agent, or Firm* — Harness, Dickey & Pierce, P.L.C.

(57) ABSTRACT

A photon-counting X-ray detector is for acquiring an X-ray image data set of an object penetrated by X-ray radiation. The detector includes a converter element, designed to convert incident X-ray radiation into an electrical signal; and a matrix with a plurality of pixel elements. At least a partial number of the plurality of pixel elements receive a signal input and at least one configurable counter is coupled to the at least a partial number of the plurality of pixel elements, for signaling. Further, the at least one configurable counter is designed to count either a pixel count signal, based on a signal directly received in each respective pixel element, or a coincidence count signal, based on the signal received directly in the respective pixel element and on a coincident signal of at least one further pixel element.

19 Claims, 6 Drawing Sheets

(51) Int. Cl.
*G01T 1/17* (2006.01)
*G01T 1/24* (2006.01)

(56) References Cited

U.S. PATENT DOCUMENTS

| | | | |
|---|---|---|---|
| 9,207,332 B2* | 12/2015 | Spahn | G01T 1/17 |
| 9,909,921 B2 | 3/2018 | Ichikawa et al. | |
| 10,024,979 B1 | 7/2018 | Viswanath et al. | |
| 2008/0265169 A1 | 10/2008 | Spartiotis et al. | |
| 2011/0210235 A1* | 9/2011 | Dierickx | G01T 1/17 |
| | | | 250/214 R |
| 2012/0161016 A1* | 6/2012 | Schmitt | G01T 1/17 |
| | | | 250/370.06 |
| 2012/0326049 A1 | 12/2012 | Hannemann et al. | |
| 2013/0028382 A1 | 1/2013 | Spahn | |
| 2014/0021354 A1 | 1/2014 | Gagnon et al. | |
| 2014/0175299 A1* | 6/2014 | Spahn | G01T 1/247 |
| | | | 250/394 |
| 2014/0270073 A1 | 9/2014 | Spahn | |
| 2015/0090893 A1 | 4/2015 | Spahn | |
| 2015/0185333 A1 | 7/2015 | Cho | |
| 2016/0282476 A1* | 9/2016 | Kappler | G01T 1/17 |
| 2017/0000431 A1 | 1/2017 | Spahn | |
| 2017/0038479 A1* | 2/2017 | Goderer | G01T 1/247 |
| 2018/0049707 A1 | 2/2018 | Ishitsu et al. | |
| 2018/0224564 A1 | 8/2018 | Fu et al. | |
| 2018/0259657 A1* | 9/2018 | Fu | G01T 7/005 |
| 2018/0292544 A1 | 10/2018 | Persson et al. | |
| 2019/0072682 A1 | 3/2019 | Cao et al. | |
| 2019/0086561 A1 | 3/2019 | Viswanath et al. | |
| 2019/0213759 A1* | 7/2019 | Lee | G01J 1/44 |
| 2021/0186439 A1 | 6/2021 | Goederer et al. | |
| 2021/0190979 A1* | 6/2021 | Goederer | G01T 1/247 |

FOREIGN PATENT DOCUMENTS

| | | |
|---|---|---|
| DE | 102011080077 A1 | 1/2013 |
| DE | 102011077859 B4 | 1/2014 |
| DE | 102012224209 A1 | 7/2014 |
| DE | 102013204264 A1 | 9/2014 |
| DE | 102015212155 A1 | 1/2017 |
| DE | 102015218585 B4 | 3/2019 |
| EP | 3839577 A1 | 6/2021 |
| EP | 3839578 A1 | 6/2021 |
| JP | 2000287104 A | 10/2000 |
| WO | WO 2018133087 A1 | 7/2018 |

OTHER PUBLICATIONS

Loeliger, T. et. al., "The New PILATUS3 ASIC with Instant Retrigger Capability", 2012 IEEE Nuclear Science Symposium and Medical Imaging Conference Record (NSS/MIC); https://doi.org/610-615.10.1109/NSSMIC.2012.6551180, 2012.

Kraft, E. et. al., "Experimental evaluation of the Pile-Up Trigger method in a revised quantum-counting CT detector", Proc. SPIE 8313, Medical Imaging 2012: Physics of Medical Imaging, 83134A; https://doi.org/10.1117/12.911231, 2012.

German Office Action dated Jun. 6, 2020.

* cited by examiner

PHOTON-COUNTING X-RAY DETECTOR AND METHOD FOR OPERATING A PHOTON-COUNTING X-RAY DETECTOR

PRIORITY STATEMENT

The present application hereby claims priority under 35 U.S.C. § 119 to European patent application number EP19217562.8 filed Dec. 18, 2019, the entire contents of which are hereby incorporated herein by reference.

FIELD

Example embodiments of the application generally relate to a photon-counting X-ray detector for acquiring an X-ray image data set of an object penetrated by X-ray radiation, a medical imaging device having a photon-counting X-ray detector and a method for operating a photon-counting X-ray detector.

BACKGROUND

Photon-counting X-ray detectors are used in a large number of imaging applications. These X-ray detectors are thus used, for example in computer tomographs in medical imaging, to generate a tomographic X-ray image of an examination region of a patient.

In particular, a photon-counting, direct-conversion X-ray detector can be used as a photon-counting X-ray detector. Incident X-ray radiation or photons can be converted in such X-ray detectors into electrical pulses by way of a suitable converter material. CdTe, CZT, $HgI_2$, GaAs or others, for example, can be used as the converter material. The electrical pulses are evaluated by an electronic evaluation unit, for example an integrated circuit (Application Specific Integrated Circuit, ASIC). In counting X-ray detectors, incident X-ray radiation is then measured by counting the electrical pulses, which are produced by the absorption of X-ray photons in the converter material. The height or also the length of a generated electrical pulse is, as a rule, also proportional to the energy of the absorbed X-ray photon. Consequently, spectral information can be extracted by comparison of the height or length of the electrical pulse with an energy threshold. Photon-counting X-ray detectors often have a plurality of settable energy thresholds for comparing the generated electrical pulses, enabling energy-resolved measurements as a function of a plurality of energy fields defined by the energy thresholds.

Use of photon-counting detectors in X-ray imaging offers a series of advantages compared to energy-integrating detectors. They thus enable a high spatial resolution and an intrinsically energy-resolved measurement.

The image quality of current photon-counting X-ray detectors is limited by the finite extent of the generated charge clouds (and by the generation of characteristic X-ray radiation) in the detector material, however. The result of this is that sometimes not all of the energy of the X-ray photon is deposited in the targeted pixel, and instead some of the energy is registered in adjacent pixels. Consequently, photons are registered under the incorrect energy on the one hand and, secondly, photons in adjacent pixels can also be counted several times (=coincidence). These coincidences not only impair the spectral properties of the detector, but also lead, quite generally, to an impairment of the DQE (detectable quantum efficiency) of the detector due to an increase in the noise and a reduction in the spatial resolution. This is an effect which degrades the image quality for all applications, therefore.

The typical circuitry-based approach to solving the problem lies in the implementation of what are known as "charge summing" circuits in the electronic evaluation unit of the detector. Here, during the detection process in the analog part of the electronic evaluation unit of a pixel, it is recognized that charge was deposited in a plurality of adjacent pixels, and the total charge of all pixels is associated with one pixel (typically the one with the most charge or the fastest increase in current). Consequently, double counts are prevented and the original charge is more or less restored. One drawback of such circuits is that the dead time of the pixels is massively increased. Consequently, the problem of the "pulse pile up" is intensified, in which the signals of a plurality of photons overlap and likewise lead to falsified measurements. A good high flux capability, such as is demanded in computer tomography, is no longer given thereby. Alternatively, the impairment of the energy resolution and DQE can be counteracted by an increase in the pixel size (for example to >0.3 mm edge length), although likewise at the cost of the high flux capability and additionally at the cost of the spatial resolution capacity.

DE 10 2011 077 859 B4 discloses, for example, a quantum-counting radiation detector with an array of detector elements, which each generate a charge quantity dependent on the energy of occurring radiation quanta and, in order to form relatively large detector units, are divided into groups of adjacent detector elements, of a first processing stage, by which, for each of the groups, one electrical signal respectively is provided, which depends on the total of the generated charge quantities of the detector elements of the group, and of a second processing stage, by which the radiation quanta impinging on the respective groups are counted by evaluation of the provided electrical signals to obtain a counting result for each group.

DE 10 2015 218 585 B4 discloses a counting X-ray detector having a macropixel with a plurality of subpixels and having an integrated circuit, with a summation circuit being provided for forming a sum signal of a whole number of K adjacent subpixels, it being possible to connect the inputs of a plurality of first discriminators to the sum signal by way of a switch, and the number K of subpixels being variably settable to form a sum signal.

"Coincidence counters for charge sharing compensation in spectroscopic photon counting detectors" by Scott S. Hsieh in IEEE Transactions on Medical Imaging. (doi: 10.1109/TMI.2019.2933986) also proposes a coincidence counter similar to existing counter based on energy fields.

SUMMARY

The inventors have discovered that limited resources (power, space, time) available in the electronic evaluation unit for such circuits always require a targeted compromise in the choice of implemented circuits and methods, however, in particular if, on the other hand, other desirable properties of the electronic evaluation unit are not to be dispensed with at the same time.

At least one embodiment of the invention provides an improved photon-counting X-ray detector for flexible use, therefore.

Further advantageous embodiments and developments of the invention, in part inventive in their own right, are presented in the claims and the following description.

At least one embodiment of the invention relates to a photon-counting X-ray detector for acquiring an X-ray image data set of an object penetrated by X-ray radiation, having a converter element designed to convert incident X-ray radiation into an electrical signal, and a matrix with a plurality of pixel elements. At least a partial number of the plurality of pixel elements in each case has a signal input and at least one configurable counter coupled thereto for signaling, wherein the configurable counter is designed to count either a pixel count signal, which is based on a signal that has been received directly in the pixel element of the partial number of the plurality of pixel elements or a coincidence count signal, which is based on the signal that has been received directly in the pixel element and on a coincident signal of at least one further pixel element of the plurality of pixel elements.

At least one embodiment of the invention also relates to a medical imaging device having an inventive photon-counting X-ray detector of at least one embodiment.

At least one embodiment of the invention also relates to a method for operating a photon-counting X-ray detector, which is designed according to one of the above-described variants, for acquiring an X-ray image data set of an object penetrated by X-ray radiation, wherein in a first counting mode the at least one configurable counter of a pixel element of the partial number of the plurality of pixel elements counts a pixel count signal, which is based on a signal that has been received directly in a respective pixel element of the partial number of the plurality of pixel elements and in a second counting mode the configurable counter of a pixel element of the partial number of the plurality of pixel elements counts a coincidence count signal, which is based on the signal that has been received directly in the respective pixel element and on a coincident signal of at least one further pixel element of the plurality of pixel elements, and wherein it is possible to switch between the first and the second counting modes.

At least one embodiment of the invention also relates to a photon-counting X-ray detector for acquiring an X-ray image data set of an object penetrated by X-ray radiation, comprising:

a converter element, designed to convert incident X-ray radiation into an electrical signal; and a matrix with a plurality of pixel elements, wherein at least a partial number of the plurality of pixel elements receive a signal input and at least one configurable counter is coupled to the at least a partial number of the plurality of pixel elements, for signaling, wherein the at least one configurable counter is designed to count either a pixel count signal, based on a signal directly received in each respective pixel element of the partial number of the plurality of pixel elements, or a coincidence count signal, based on the signal received directly in the respective pixel element and on a coincident signal of at least one further pixel element of the plurality of pixel elements.

At least one embodiment of the invention also relates to a method for operating a photon-counting X-ray detector for acquiring an X-ray image data set of an object penetrated by X-ray radiation, comprising:

counting, in a first counting mode of at least one configurable counter of a respective pixel element of a partial number of the plurality of pixel elements of the photon-counting X-ray detector, a pixel count signal, based on a signal received directly in the respective pixel element of the partial number of the plurality of pixel elements; and counting, in a second counting mode of the at least one configurable counter of the respective pixel element, a coincidence count signal, based on the signal received directly in the respective pixel element and on a coincident signal of at least one further pixel element of the plurality of pixel elements, the at least one configurable counter being switchable between the first and the second counting modes.

BRIEF DESCRIPTION OF THE DRAWINGS

The invention will be explained below based upon example embodiments with reference to the accompanying figures. The representation in the figures is schematic, highly simplified and not necessarily to scale. In the drawings.

DETAILED DESCRIPTION OF THE EXAMPLE EMBODIMENTS

Figure 1:
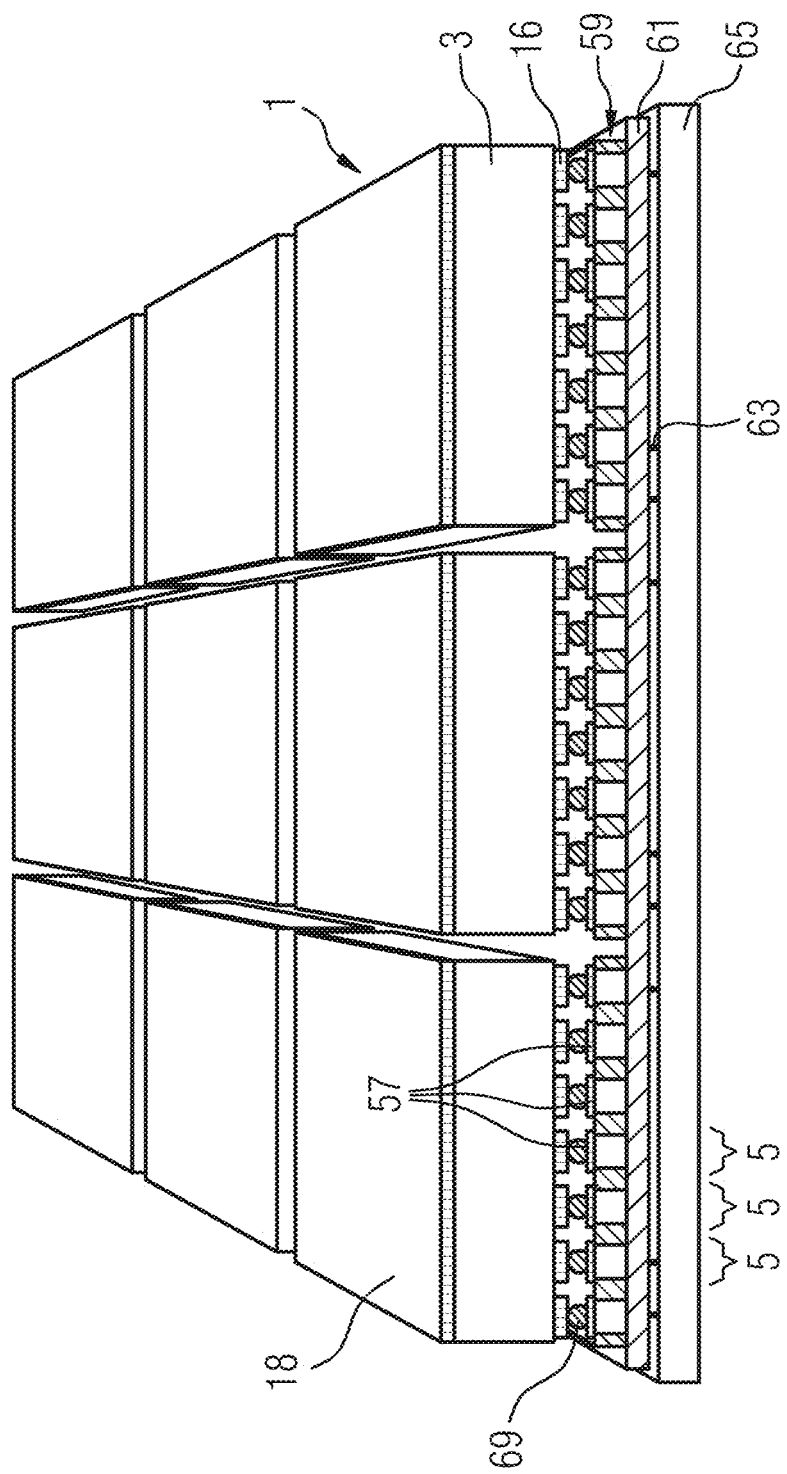
FIG. 1 shows an example detector module with a photon-counting X-ray detector.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/ DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a photon-counting X-ray detector for acquiring an X-ray image data set of an object penetrated by X-ray radiation, having a converter element designed to convert incident X-ray radiation into an electrical signal, and a matrix with a plurality of pixel elements. At least a partial number of the plurality of pixel elements in each case has a signal input and at least one configurable counter coupled thereto for signaling, wherein the configurable counter is designed to count either a pixel count signal, which is based on a signal that has been received directly in the pixel element of the partial number of the plurality of pixel elements or a coincidence count signal, which is based on the signal that has been received directly in the pixel element and on a coincident signal of at least one further pixel element of the plurality of pixel elements.

The photon-counting X-ray detector used within the framework of at least one embodiment of the invention can also be referred to as a counting or direct conversion X-ray detector. Direct conversion X-ray detectors are usually implemented in a stack formation in which an assigned evaluation unit, for example in the form of an ASIC (Application Specific Integrated Circuit), is fastened at the bottom to a layer of the converter material, in other words, to the converter element. In addition, an intermediate layer, an interposer, can optionally be arranged between the evaluation unit and the converter element, and this can be used for stability or also for redirecting signal cables. The bottom of the converter element conventionally has a plurality of electrodes, also called sensor pixel electrodes below, in the form of metallized contact elements in a matrix.

The evaluation unit is connected, conventionally soldered, thereto for signaling. Conventionally, one pixel-like counter-contact element respectively, also called pixel electrode below, opposes a converter-side contact element on the side of the evaluation unit. The evaluation unit conventionally provides pixel-by-pixel pixel electronics for pixel-by-pixel processing of a signal that has entered via the pixel electrodes. Incident X-ray radiation is converted in the converter material of the converter element as a function of the locally deposited energy of an X-ray photon into charge carriers, based on which a signal, conventionally an electrical pulse, is generated in the pixel-by-pixel pixel electronics, and is conventionally processed further pixel-by-pixel.

An inventive pixel element can hereinafter be taken to mean, in particular, the pixel-by-pixel pixel electronics, in other words, electronics pixels, of the evaluation unit, which is coupled for signaling to the converter element via the pixel electrode, and further processes the signals entering from the converter element via the respective pixel electrode. A corresponding detection volume in the converter element is associated with the pixel element, and this is formed by the electrical field between a respective sensor pixel electrode and a top electrode, which is attached to the opposite side of the converter element and which forms the sensitive detection volume of a pixel element.

Conventionally, the electrical pulse generated in a pixel element, whose height or also length corresponds to the deposited energy of the X-ray quantum in the detection volume of the pixel element, is registered as a counting event and filed in a digital storage unit of a counting element, in other words, counted as a pixel count signal if the pulse lies above a defined threshold value, in other words, essentially an energy threshold. This essentially means that in this case the count of the counting element associated with the threshold value is increased by one counting unit. In the case where two, three or more threshold values are introduced, the generated electrical signal, in accordance with the predefined threshold values, can be counted by one or more counting element(s).

If a distribution of the deposited energy of an event among two or more pixel elements occurs as a result of charge sharing or fluorescence, signals can be essentially simultaneously generated accordingly in more than one pixel element and multiple counts, in other words, coincidences, can occur thereby. In this case a signal that has been received directly in one pixel element of the plurality of pixel elements and coincidentally a signal in at least one further pixel element of the plurality of pixel elements consequently occurs. Signals that occur coincidentally are then, in particular, those which occur within a very short, optionally definable, time window both in a pixel element being considered and in a further pixel element. These can then be deemed to be associated with higher probability with an individual photon event.

At least one embodiment of the inventive X-ray detector accordingly has a plurality of pixel elements, wherein at least one partial number thereof is provided with a configurable counter, which optionally, depending on the configuration of the counter, counts either pixel count signals or coincidence count signals. The configurable counter is configurable in respect of a first counting mode, therefore in which pixel count signals are counted, and in respect of a second counting mode in which coincidence count signals are counted. The configurable counter can have a first and a second setting, so in a first setting of the configurable counter in each case the signal that has been received directly in a pixel element is registered as a counting event and is counted as a pixel count signal, and in a second setting of the configurable counter a counting event is registered based upon the signal that has been received directly and a signal that occurred coincidentally in at least one further pixel element and is counted as a coincidence count signal.

The at least one further pixel element, on which a coincidence count signal is based, can preferably comprise at least one directly adjacent pixel element of the respective pixel element. It can, however, also be a pixel element that is not directly adjacent.

Preferably, a respective pixel element of the partial number of the plurality of pixel elements is also designed to count, via the configurable counter coincidence, count signals, which are based on the signal that has been received directly in the respective pixel element of the partial number of the plurality of pixel elements and on at least one coincident signal of a plurality of further pixel elements, for example 2, 3, 4, 8 or 24, of the plurality of pixel elements.

The configurable counter can have, in particular, a controllable switching element for activation of the first or the second setting of the configurable counter for this purpose. The configurable counter can be controlled, for example automatically, as a result and either the first or the second setting can be activated. Similarly, a manual activation can also be provided. Control can take place in conjunction with one or more parameter(s). For example, the parameter can comprise X-ray flux information, a position parameter of a respective pixel element, an object parameter or an application parameter of the medical application, in the framework of which the X-ray image data set is acquired. The at least one configurable counter can in each case be configurable before or also during acquisition of the X-ray image data set.

In addition to a controllable switching element, the configurable counter can also comprise a counting element. The counting element can be designed, in particular, to count a number of pixel counter signals or coincidence count signals and to store them at least temporarily.

At least a partial number of the plurality of pixel elements has at least one configurable counter. For example, only every second or third pixel element in the matrix of pixel elements has at least one configurable counter. Every pixel element of the plurality of pixel elements can also have at least one configurable counter, however. This means that the at least one partial number can also comprise the entirety of the plurality of pixel elements of the X-ray detector, so each pixel element of the plurality of pixel elements has at least one configurable counter in each case.

The pixel elements of the partial number of the plurality of pixel elements can similarly also have more than one configurable counter, for example two or three. In particular, the plurality of configurable counters can each be linked with a settable threshold value, in other words, an energy threshold. In addition to the at least one configurable counter, a pixel element of the partial number of the plurality of pixel elements can also have at least one non-configurable counter. A non-configurable counter comprises at least one counting element and can be designed, in particular, to count a signal that has been received directly in a pixel element as a pixel count signal.

The X-ray image data set acquired via the photon-counting X-ray detector can be based on the pixel count signals and/or the coincidence count signals. The pixel count signals and/or coincidence count signals can also be processed further for this. If, for example, both pixel count signals and coincidence count signals are present, the counted coincidence count signals can be used to correct counted pixel count signals or X-ray images based thereon and consequently make an X-ray image data set with improved image quality possible.

Advantageously, the invention enables flexible use of the X-ray detector coordinated with the needs of acquisition of an X-ray image data set. With a suitable configuration of the at least one configurable counter of the partial number of the plurality of pixel elements, counting of count events can thus be enabled to which only those X-ray quanta, which directly reached the pixel element (or the region of the X-ray converter with which the pixel element is associated), contribute. Similarly, a suitable configuration of the at least one configurable counter of the partial number of the plurality of pixel elements can enable counting in which coincidentally impinging X-ray quanta, for example adjacent pixel elements, are also incorporated. This means that, coordinated with the requirements in respect of acquisition of the X-ray image data set, advantageously, coincidence information can be gathered only in the cases where it enables a positive influence on a resulting image quality. In other cases, in which coincidence information does not have a positive effect, or has only a slight one, it is possible to fall back on the configurable counter as the "regular" counter, however. Advantageously, this enables flexible use of the X-ray detector and an optimum resource-saving implementation of the pixel elements. An even more flexible adjustment of the X-ray detector can be achieved if a plurality of configurable counters are available in a respective pixel element.

In one embodiment of the photon-counting X-ray detector, the at least one configurable counter has a configurable multiplexer, which has at least one first and one second setting, wherein in the first setting the pixel count signal is counted via the configurable counter, and wherein in the second setting the coincidence count signal is counted via the configurable counter.

The integration of a configurable multiplexer as a switching element represents a particularly advantageous and simple implementation of the inventive configurable counter. A multiplexer is essentially a selection circuit with which one input signal from a number of input signals can be selected and be connected through at an output of the multiplexer. The configurable multiplexer can be connected upstream of a counting element of the configurable counter. This means the configurable multiplexer serves as an input multiplexer of the counter, wherein in the first setting of the multiplexer the pixel count signal is counted and stored via the counting element based on the signal that has been received directly in each pixel element of the partial number of the plurality of pixel elements and wherein in the second setting of the multiplexer the coincidence count signal is counted and stored based on the signal that has been received directly in the respective pixel element and on a coincident signal of at least one further pixel element of the plurality of pixel elements.

It can also be provided that further input signals are provided at the multiplexer, so more than two settings of the configurable counter can be configured. For example, a signal based on different further pixel elements can in each case serve as a further input signal or the output signal of a summation circuit provided in the pixel elements, which totals the signals of a plurality of pixel elements of the plurality of pixel elements, can also serve as an input signal of the multiplexer, wherein, depending on the setting of the multiplexer, one of the input signals is connected through.

Furthermore, in one variant embodiment it can be provided that the at least one configurable counter can be configured individually for each pixel element of the partial number of the plurality of pixel elements and/or in each case jointly for a group of pixel elements of the partial number of the plurality of pixel elements.

Advantageously, for each pixel element or for a group of pixel elements, the setting most favorable to the image quality can be set for acquisition of the X-ray image data set, so the optimum image quality can always be achieved via the X-ray detector. Advantageously, a joint configuration can be enabled in groups in a time-efficient manner.

A group can in each case define, for example, a macropixel comprising a plurality of pixel elements. A group of pixel elements can in each case be defined by the position of a respective pixel element relative to a scattered radiation collimator or the like. A group can also comprise, for example, all pixel elements arranged at the edge of the matrix or all pixel elements arranged centrally in the matrix. Pixel elements arranged at the edge are, in particular, not bordered on all sides of a pixel element by adjacent pixel elements so a different configuration of the configurable counter, in contrast to the pixel elements arranged centrally, can optionally be advantageous here. The group of pixel elements can also comprise the whole partial number and accordingly also the whole plurality of pixel elements, wherein less flexibility but a particularly simple implementation can be achieved.

An advantageous practical variant embodiment of the inventive photon-counting X-ray detector comprises that each pixel element of the plurality of pixel elements has a conversion apparatus connected to the signal input, with at least one signal amplifier and a number of comparators, each with a settable threshold value, and wherein for each pixel element of the partial number of the plurality of pixel elements, at least one comparator of the number of comparators is coupled for signaling to the at least one configurable counter.

The signal converted in the converter element into electrical charge and fed into a pixel element of the electronic evaluation unit via the pixel electrode is amplified with the aid of the signal amplifier and counted if the amplified signal lies above the settable threshold value of the comparator. In other words, if the amplified signal lies above the settable energy threshold of the comparator, an output signal is provided at the signal output of the comparator, which can be counted via a counting element coupled thereto. In this way only those signals, which exceed the threshold value, so noise is suppressed, are counted or only those events with energy levels above a desired threshold value are counted. Each pixel element of the plurality of pixel elements can have a plurality of comparators each with a settable threshold value, wherein the output signal of each comparator can be linked to a counting element for counting the pixel count signals. Energy-selective imaging is thus possible.

Inventively, at least a partial number of the plurality of pixel elements has at least one configurable counter. This means that at least one comparator of each pixel element of the partial number of the plurality of pixel elements is coupled for signaling to a configurable counter. If a plurality of comparators is present, each of the comparators of the partial number of the plurality of pixel elements can be interconnected to a configurable counter. Consequently, optimum flexibility can be achieved. It is also possible, however, for only some of the comparators of a pixel element of the partial number of the plurality of pixel elements to be linked for signaling to a configurable counter. The remainder of the comparators can be linked for signaling to a "regular" counting element for counting pixel count signals, as described above. Consequently, the signaling complexity and the power consumption can be reduced.

According to a further embodiment of the inventive photon-counting X-ray detector advantageous for a practical implementation, each pixel element of the partial number of the plurality of pixel elements also has at least one coincidence logic, which is coupled for signaling to at least one comparator of the respective pixel element of the partial number of the plurality of pixel elements and to at least one comparator of the at least one further pixel element of the plurality of pixel elements, wherein the coincidence count signal is based on an output signal of the coincidence logic.

The coincidence logic can also be referred to as a digital coincidence circuit. The coincidence logic of a pixel element of the partial number of the plurality of pixel elements is connected in each case to at least one comparator of the respective pixel element of the partial number of the plurality of pixel elements and to at least one comparator of the at least one further pixel element of the plurality of pixel elements. The at least one further pixel element of the plurality of pixel elements does not necessarily have to be, but can also be, a pixel element of the partial number of the plurality of pixel elements with a configurable counter. The coincidence logic can be designed, in particular, to provide an output signal on the occurrence of coincident signals in the pixel element being considered of the partial number of the plurality of pixel elements and the at least one further pixel element of the plurality of pixel elements, which output signal can be counted as a coincidence count signal via a counter coupled for signaling to the coincidence logic. This means that it is possible to check whether—starting from a pixel element of the partial number of the plurality of pixel elements—at least the one further linked pixel element has likewise detected a counting event above a given threshold value. Based on the output signals of the comparators coupled for signaling to the coincidence logic, a coincidence signal is then generated in the case of coincident events. The coincidence count signal of the coincidence logic can then be counted accordingly as a pixel count signal in the second setting of the configurable counter.

The output signal of the coincidence logic of a pixel element of the partial number of the plurality of pixel elements can correspond, in particular, to a first input signal of a configurable multiplexer of a configurable counter. The output signal of a comparator of the pixel element of the partial number of the plurality of pixel elements can correspond, in particular, to a second input signal of the configurable multiplexer. Depending on the configuration of the configurable multiplexer, either the output signal of the comparator or the output signal of the coincidence logic can be provided as the output signal of the multiplexer and be counted via the counting element coupled to the multiplexer.

In one variant embodiment of the inventive photon-counting X-ray detector, each pixel element of the plurality of pixel elements has a plurality of comparators, and wherein the at least one coincidence logic of a pixel element of the partial number of the plurality of pixel elements is coupled for signaling to more than one comparator of the at least one further pixel element of the plurality of pixel elements.

For example, two or more comparators of the further pixel element can be coupled for signaling to the coincidence logic of a pixel element of the partial number of the plurality of pixel elements. For example, it can be provided in this case that it is possible to select which output signal of the coupled comparators of the further pixel element contributes to a coincidence count signal in the respective pixel element of the partial number of the plurality. In this case, advantageously, easily switchable coincidence information can optionally be gathered as a function of differently set threshold values.

For example, in this case a respective pixel element of the partial number of the plurality of pixel elements has a further controllable switching element, for example a further multiplexer, which is coupled for signaling to more than one comparator of the at least one further pixel element. Depending on the setting of the switching element, a selected output signal of the coupled comparators can then be provided as the output signal of the switching element and serve as the basis of a coincidence count signal.

Furthermore, in one variant embodiment of the invention it can be provided that each pixel element of the partial number of the plurality of pixel elements has at least one setting element for runtime adjustment or for delaying an input signal in the at least one coincidence logic.

Advantageously, the output signals of those comparators of the respective pixel element and of the at least one further pixel element, which serve as input signals of the coincidence logic, can be coordinated with each other and be optimized for the coincidence logic. Advantageously, different cable lengths when supplying the signals can be compensated. In one advantageous embodiment, each of the input signals is linked in the coincidence logic to such a setting element.

In one advantageous embodiment, the at least one setting element is configurable, in other words, can be controlled and adjusted even after implementation of the circuit. In this way differences between the signal inputs can advantageously also still be subsequently compensated and optimized.

In one variant embodiment of the inventive photon-counting X-ray detector, each pixel element of the partial number of the plurality of pixel elements has a plurality of configurable counters, which is in each case coupled for signaling to at least one comparator of the respective pixel element of the partial number of the plurality of pixel elements and to at least one comparator of the at least one further pixel element of the plurality of pixel elements.

The flexibility of the pixel elements can be advantageously increased by the provision of a plurality of configurable counters. In particular, the configurable counters of a pixel element can in each case be designed to be individually configurable. Depending on the medical application, a balance between the necessary spectral resolution and the extent of the gathered coincidence information can advantageously be carried out via the X-ray detector.

According to a further embodiment of the inventive photon-counting X-ray detector, the coincidence count signal is based on the signal that has been received directly in the respective pixel element of the partial number of the plurality of pixel elements and on coincident signals of between one and 24 further pixel elements of the plurality of pixel elements.

This means that the respective pixel element is designed to form and count a coincidence count signal if a coincident signal occurs at least in one of the one to 24 further pixel elements.

The one to 24 further pixel elements, preferably in a matrix-like arrangement of the plurality of pixel elements, can be part of the directly adjacent pixel elements, diagonally adjacent pixel elements or the next but one neighbor.

Preferably, the at least one further pixel element comprises a directly adjacent pixel element of the respective pixel element of the partial number of the plurality of pixel elements. For example, coincidence count signals are expediently formed in each pixel element of the plurality of pixel elements at least with the four directly adjacent further pixel elements of the plurality of pixel elements. A directly adjacent pixel element of a pixel element being considered of the partial number of the plurality of pixel elements can correspond, in particular, to a pixel element of the plurality of pixel elements, which, in a pixel grid defined by the matrix-like arrangement of the plurality of pixel elements, has a common edge with the pixel element being considered. For example, as an alternative or in addition, coincidence count signals can be formed based upon one or all diagonal adjacent pixel elements. Advantageously, at least with those further pixel elements, coincidence count signals are counted in which coincident signals occur with high probability. This can comprise at least the four directly adjacent pixel elements or the four directly adjacent pixel elements together with the diagonally adjacent pixel elements.

A different choice and/or number of further pixel elements can also be provided, however. For example, next but one neighbors, in other words, adjacent pixel elements of the directly adjacent pixel elements of the pixel element being considered, can be considered in respect of coincident signals. Consideration and incorporation of next but one neighbors can be advantageous in particular when it is provided that the signals of a plurality of pixel elements are combined, or with small pixel sizes in which coincident signals should be expected to a relatively large extent even beyond the distances predefined by the pixel elements. A higher number of further pixel elements also involves more complex interconnection of the pixel elements among themselves, however.

The number and choice of further pixel elements, on which the coincidence count signal is based, can vary within the partial number of the plurality of pixel elements and/or have a configurable design, so, following provision of the X-ray detector, the number and choice of further pixel elements can be selected.

In one embodiment of the photon-counting X-ray detector, the number and/or choice of further pixel elements of the plurality of pixel elements, on which the coincidence count signal is based, is different for different pixel elements.

Advantageously, a particularly flexible configuration of the X-ray detector can be enabled. Advantageously, different boundary conditions of the individual pixel elements can be taken into account here. Different boundary conditions can exist, for example due to the arrangement of the pixel elements relative to each other within a pixel matrix or due to the arrangement of the pixel elements relative to an external element, for example a scattered rays grid or otherwise. It can thus be provided that pixel elements whose detection volume is, for example, partially shaded at one side by a scattered rays grid, do not count coincidence count signals based on the adjacent further pixel element at this side since here, owing to the shading, fewer impairments due to coincidences that occur can be expected. It can also be provided, for example, that the plurality of pixel elements is divided into macropixels, which in each case corresponds to a group of pixel elements. For example, only coincidence count signals between pixel elements within a group are counted in this case. Depending on the arrangement of a pixel element within the macropixel group, the number and/or choice of further pixel elements can then advantageously be selected to be different.

In one embodiment, the number and/or choice of further pixel elements of the plurality of pixel elements, on which the coincidence count signal for a pixel element arranged at the edge of the matrix of pixel elements and with fewer adjacent pixel elements is based, can in particular be different from the number and/or choice of further pixel elements of the plurality of pixel elements, on which the coincidence count signal for a pixel element arranged centrally in the matrix of pixel elements is based.

Advantageously, a particularly flexible configuration of the X-ray detector can be enabled. Advantageously, different boundary conditions of the individual pixel elements, which are arranged centrally or at the edge, can be taken into account here.

In one variant embodiment of the inventive photon-counting X-ray detector, each pixel element of the partial number of the plurality of pixel elements also comprises at least one electronic element for preventing paralysis of the at least one configurable counter.

Advantageously, the high-flux behavior of the pixel elements of the partial number of the plurality of pixel elements can be improved. The electronic element for preventing paralysis can be arranged upstream or also downstream circuitry-wise of a configurable switching element, for example a multiplexer. At least one electronic element for preventing paralysis can also be provided for a respective signal input of a coincidence logic. An electronic element of this kind for preventing paralysis can induce further count events, for example in the case of a comparator threshold being permanently exceeded.

At least one embodiment of the invention also relates to a medical imaging device having an inventive photon-counting X-ray detector of at least one embodiment.

The features and advantages of the photon-counting X-ray detector can be transferred directly to the medical imaging device.

The medical imaging device can be designed, in particular, as a medical X-ray apparatus. The medical imaging device can comprise, in particular, an X-ray source associated with the photon-counting X-ray detector. Conventionally, the medical imaging device comprises at least one inventive photon-counting X-ray detector and, facing it, at least one X-ray source, for example an X-ray tube. For the acquisition of the X-ray image data set, the object to be imaged can then be positioned in particular between the X-ray source and the photon-counting X-ray detector and be penetrated via the X-ray source.

In particular, the medical imaging device can be designed as a computed tomography system. It can also be designed, for example, as a C-arm X-ray apparatus and/or Dyna-CT or otherwise, however.

At least one embodiment of the invention also relates to a method for operating a photon-counting X-ray detector, which is designed according to one of the above-described variants, for acquiring an X-ray image data set of an object penetrated by X-ray radiation, wherein in a first counting mode the at least one configurable counter of a pixel element of the partial number of the plurality of pixel elements counts a pixel count signal, which is based on a signal that has been received directly in a respective pixel element of the partial number of the plurality of pixel elements and in a second counting mode the configurable counter of a pixel element of the partial number of the plurality of pixel elements counts a coincidence count signal, which is based on the signal that has been received directly in the respective pixel element and on a coincident signal of at least one further pixel element of the plurality of pixel elements, and wherein it is possible to switch between the first and the second counting modes.

In addition, further pixel count signals and/or coincidence count signals based on further configurable and/or regular, non-configurable counters can also be counted.

The X-ray detector is associated with an X-ray source for radiating X-ray radiation.

For example, in a first configuration of the partial number of the plurality of pixel elements, the X-ray detector can be provided such that the configurable counter of a respective pixel element of the partial number of the plurality of pixel elements is configured either for the first counting mode or for the second counting mode.

For example, configuring of the photon-counting X-ray detector can be carried out, wherein at least for some of the pixel elements of the partial number of the plurality of pixel elements the counting mode is switched to in that the at least one configurable counter of at least some of the pixel elements of the partial number of the plurality of pixel elements is switched.

Furthermore, a pixel-by-pixel conversion of the X-ray radiation penetrating the object and impinging the X-ray detector into electrical signals in the pixel elements can be provided. Furthermore, a respective pixel element of the partial number of the plurality of pixel elements can be provided with a conversion of the electrical signals into pixel count signals or into coincidence count signals, depending on configuration and interconnection of the pixel elements, and storing of the counted numbers in the pixel elements. Reading-out of the counted numbers of pixel count signals and/or coincidence count signals and creation of one of more image data set(s) representing the object can then be provided.

It can also be provided that with at least one embodiment of the inventive method, configuring is dependent on one or more parameter(s) of the medical imaging device with which the inventive X-ray detector is associated and/or to which it is structurally connected and/or on the X-ray application. For example, the variant of the settings most favorable to the image quality can be configured for each pixel element individually or in each case for groups of pixel elements, so the optimum image quality can always be achieved. The parameter(s) can be retrieved, for example, from a memory or a system controller of the medical imaging device or else be directly determined or measured. For example, the method comprises the retrieval and/or determination of one or more parameter(s).

Configuring can be carried out automatically via the control unit. If required, manual activation or control can also be provided. Automatic control can occur in connection with the determined parameter(s). Retrieval and/or determination can also be carried out in particular automatically for this via a control unit and be applied for configuring.

According to one embodiment of the invention, the parameter is formed by the level of an X-ray flux of the X-ray source of the X-ray system. In such a case it can be provided, for example, that, for all pixel elements of the partial number of the plurality of pixel elements, above a certain threshold value of the X-ray flux, the first setting of the at least one configurable counter is set and below the threshold value, the second setting is set.

For example on determining a particularly high X-ray flux (for example due to a retrieval from the system controller or due to a measurement), where gathering of coincidence information is possibly no longer meaningful, the configurable counter can be configured to count only the pixel count signals, therefore. With an average or low X-ray flux, configurable counters can then be configured to count coincidence count signals. A controller can also be provided that is dependent, for example, on the anticipated count rate (dose/unit of time) for the application.

In this way, with high X-ray fluxes, errors due to incorrect coincidences are avoided, whereas, with low X-ray fluxes, the coincidences can also be taken into account.

Within the framework of at least one embodiment of the invention, features, which are described in relation to different embodiments of the invention and/or different categories of claim (method, use, device, system, arrangement, etc.), can be combined to form further embodiments of the invention. For example, a claim, which relates to a device, can also be developed with features, which are described or claimed in connection with a method, and vice versa. Functional features of a method can be implemented by appropriately designed, concrete components. In addition to the embodiments of the invention explicitly described in this application, a wide variety of further embodiments of the invention are conceivable, which a person skilled in the art can arrive at without departing from the scope of the invention as it is predefined by the claims.

Use of the indefinite article "a" or "an" does not preclude the relevant feature from also being present several times. Use of the expression "has/have" does not preclude the terms linked by way of the expression "has/have" from being identical. For example, the medical imaging device has the medical imaging device. Use of the expression "unit" does not preclude the subject matter to which the expression "unit" refers from having a plurality of components, which can be spatially separated from each other.

In the context of the present application the expression "based on" can be understood, in particular, within the meaning of the expression "using". In particular, wording, which is generated (alternatively: ascertained, determined, etc.) according to a first feature based on a second feature does not preclude the first feature from being generated (alternatively: ascertained, determined, etc.) based upon a third feature.

FIG. 1 shows an example embodiment of a detector module 51 with a plurality of inventive X-ray detectors 1. In a preferred embodiment the detector module 51 has a two-dimensional matrix or arrangement of a plurality of X-ray detectors 1. A respective X-ray detector 1 in turn has a plurality of pixel elements 5 in a matrix-like arrangement, so spatially resolved measurements can be provided.

A respective X-ray detector 1 in the illustrated example has a converter element 3. The converter element 3 can be designed as a planar direct converter, for example having CdTe, CZT, CdZnTeSe, CdTeSe, CdMnTe, InP, TlBr$_2$, HgI$_2$, GaAs, Si or another as the converter material. The top of the converter element 3 has a first electrode 18 (top electrode). The bottom of the converter element 3 has sensor pixel electrodes 16. The sensor pixel electrodes 16 are connected by the electrically conductive connections 69 and the pixel electrodes 57 to the pixel elements 5 in the evaluation unit 59. The evaluation unit can be designed, for example, in the form of an ASICS. The electrically conductive connections 69 can be designed, for example, as bump bonds or solder material in connection with copper pillars or also in some other way. The shared number of sensor pixel electrodes 16, the number of conductive connections 69, the number of pixel electrodes 57 and the number of pixel elements 5 in the evaluation unit 59 are usually equal. An electrical field between the first electrode 18 and a sensor pixel electrode 16 determines a sensitive detection volume in the converter element 3 associated with a pixel element 5, which is formed, in particular in each case, by an electrical field between the sensor pixel electrodes 16 and the top electrode 18.

In the illustrated example the evaluation unit 59 is arranged on a substrate 61 and is connected to a peripheral electronic device 65, for example by TSV connections 63 ("Through Silicon Via" connections) through the substrate 61, to a peripheral electronic device 65.

Furthermore, the X-ray detector 1 or the X-ray detector module 51 can also comprise yet further components (not shown here).

Conventionally, the electrical pulse generated in a pixel element 5, whose height or also length corresponds to the deposited energy of the X-ray quantum in the respective detection volume of the pixel element 5, is registered as a counting event and filed in a digital storage unit of a counting element 13, in other words, registered as a pixel count signal and counted accordingly if it lies above a defined threshold value THR, in other words, essentially an energy threshold. An event is counted in that a count of the counting element 13 is incremented by one counting unit if the generated signal lies above the settable threshold value THR.

The settable threshold value THR is conventionally settable by a comparator 19. The threshold value THR can in principle also be permanently specified in analog form but is generally applied by, for example, a DAC (digital-to-analog converter). The threshold value THR can thereby conventionally be variably set at least in a certain energy field. The threshold value THR can either be set pixel-by-pixel locally (via the comparator and the DAC), for groups of pixel elements or globally in the X-ray detector 1 for all pixel elements 5 of the X-ray detector 1. In the case where two, three or more settable threshold values THR are provided in one pixel element 5 for energy-resolved measurements, the generated electrical signal is filed, in other words, counted, according to the different, pre-defined threshold values THR in one or more counting element(s) 13, which are each linked to an energy threshold THR.

At least one partial number of the plurality of pixel elements 5 of the inventive X-ray detector 1 inventively has at least one configurable counter 9 coupled for signaling to a signal input 7, by which the electrical signal is fed from the converter element 3 into the pixel element 5. The configurable counter 9 is designed either to count a pixel count signal, which is based on a signal that has been received directly in a respective pixel element 5 of the partial number of the plurality of pixel elements 5 or a coincidence count signal, which is based on the signal that has been received directly in the respective pixel element 5 and on a coincident signal of at least one further pixel element 5 of the plurality of pixel elements 5.

The configurable counter can have, in particular, a controllable switching element 11 for configuration of the configurable counter 9 and a counting element 13 coupled thereto.

The switching element 11 can be designed, in response to a control command from a control unit 53, to configure the configurable counter 9 either in the first setting for counting the pixel count signals or in the second setting for counting the coincidence count signals. The at least one configurable counter 9 can be individually configurable for each pixel element 5 of the partial number of the plurality of pixel elements 5 and/or can be jointly configurable in each case for a group of pixel elements 5 of the partial number of the plurality of pixel elements 5.

Inventively, at least one partial number of the plurality of pixel elements 5 has at least one configurable counter 9. The pixel elements 5 of the partial number of the plurality of pixel elements 5 can similarly also have more than one configurable counter 9, for example two or three. In addition to the at least one configurable counter 9, a pixel element of the partial number of the plurality of pixel elements 5 can also have at least one non-configurable counter. In addition to pixel elements configurable in this way, the X-ray detector can also have non-configurable pixel elements.

Figure 2:
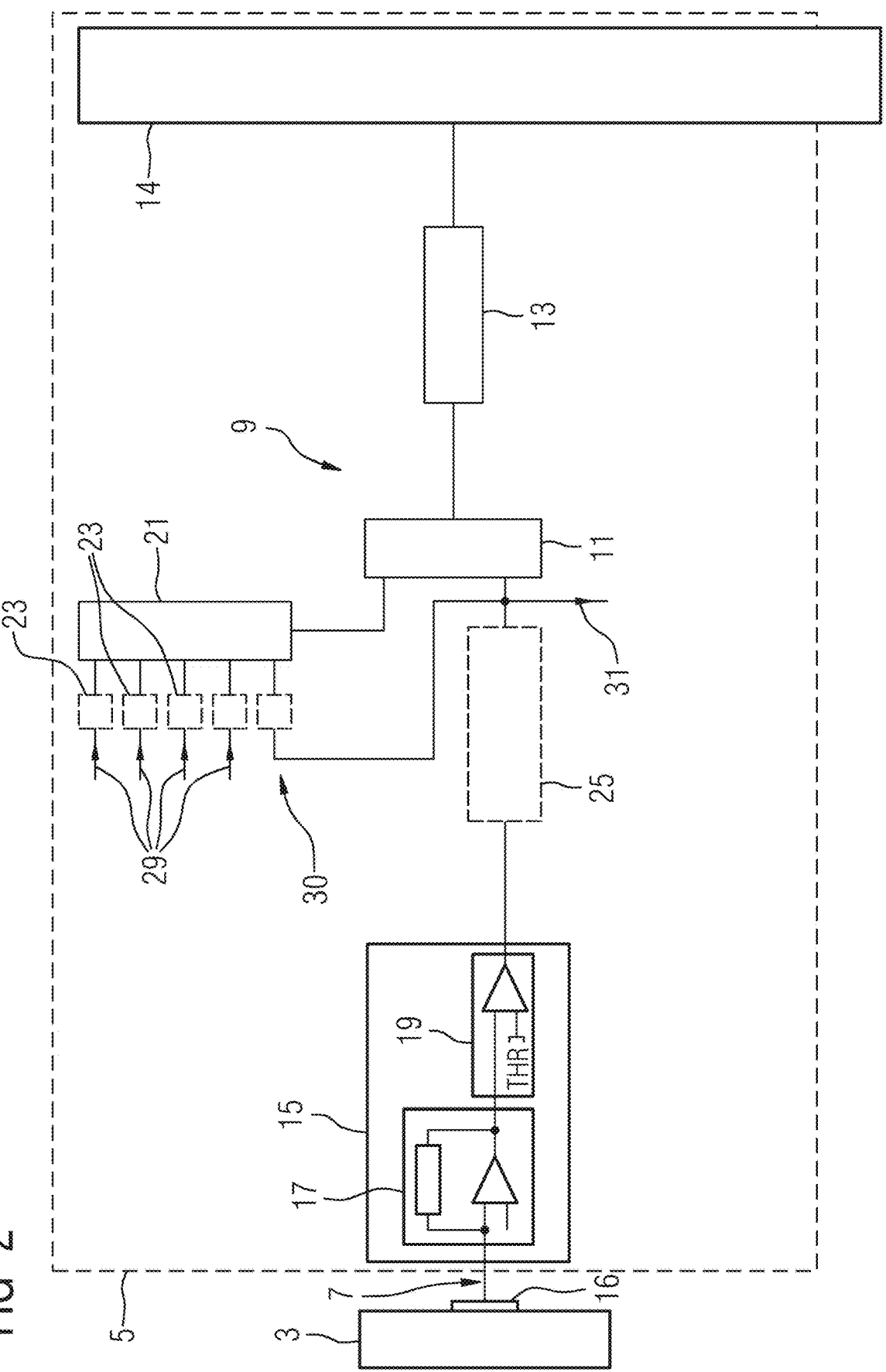
FIG. 2 shows a diagram as an illustration of an interconnection for signaling of a pixel element according to a first variant embodiment.

FIG. 2 shows a diagram as an illustration of an interconnection for signaling of a configurable pixel element 5 of the partial number of the plurality of pixel elements 5 of a photon-counting X-ray detector 1 according to a first variant with a configurable counter 9. By way of example, only a single pixel element 5 of the partial number of the plurality of pixel elements 5 is shown. The interconnection can be easily transferred to further pixel elements 5 as well, however.

The signal input 7 of the pixel element is coupled for signaling via the sensor pixel electrode 16 to the sensitive detection volume in the converter element 3 associated with the pixel element 5. For an advantageous practical implementation the pixel element 5 shown here of the partial number of the plurality of pixel elements 5 also has a conversion apparatus 15 coupled for signaling to the signal input 7, comprising at least one signal amplifier 17 for amplification of the signal generated by the incident X-ray radiation and comprising at least one comparator 19. The amplified signal is compared via the comparator 19 with a settable threshold value THR. If the amplified signal exceeds the threshold value THR of the comparator 19 a pixel count signal is generated at the signal output of the comparator 19, which is based on the signal that has been received directly in a pixel element 5 via the signal input.

The signal output of the comparator 19 is also coupled for signaling to the configurable counter 9. According to an advantageous variant, the configurable counter 9 comprises a configurable multiplexer 11 and a counting element 13 coupled to the signal output of the multiplexer 11. In a first setting of the multiplexer 11 the output signal of the comparator 19, in other words, the pixel count signal, is passed to the counting element 13, which counts the number of pixel count signals that have been received and stores them at least temporarily.

Furthermore, the pixel element 5 shown here of the partial number of the plurality of pixel elements 5 has a coincidence logic 21. The coincidence logic 21 implemented here by way of example is firstly linked for signaling via a signal input 30 likewise to the signal output of the comparator 19 of the pixel element 5 shown here. The coincidence logic 21 is also coupled for signaling to at least one further pixel element 5 of the plurality of pixel elements 5 via a signal input 29 of the coincidence logic 21. In the example shown here the coincidence logic 21 has four further signal inputs 29. In particular, in this example each of the four signal inputs 29 is coupled for signaling to a further pixel element 5 of the plurality of pixel elements 5. The coincidence logic 21 is designed to form a coincidence count signal, which is based on the signal that has been received directly in the pixel element 5 of the plurality of pixel elements 50 and on a coincident signal of at least one further linked pixel element 5 of the plurality of pixel elements 5.

The, in this example, four further pixel elements 5 of the plurality of pixel elements 5 can comprise, for example, the four directly adjacent pixel elements of the pixel element 5 being considered. A different number or choice of pixel elements 5 of the plurality of pixel elements 5 can also be coupled for signaling to the coincidence logic 21, however. For example, in addition to the directly adjacent pixel elements 5, the diagonally adjacent pixel elements 5 of the respective pixel element 5 of the partial number of the plurality of pixel elements 5 can also be coupled to the coincidence logic. Preferably, the coincidence count signal is generally based on the signal that has been received directly in the respective pixel element 5 of the partial number of the plurality of pixel elements 5 and on coincident signals of between one and 24 further pixel elements 5 of the plurality of pixel elements 5. The coincidence count signal is particularly preferably based on coincident signals of between 1 and 8 further pixel elements 5 of the plurality of pixel elements 5.

In particular, the number and/or choice of further pixel elements 5 of the plurality of pixel elements 5, on which the coincidence count signal of a respective pixel element 5 of the partial number of the plurality of pixel elements 5 is based can be different for different pixel elements 5 of the plurality of pixel elements 5.

In one variant embodiment, in particular the number and/or choice of further pixel elements 5 of the plurality of pixel elements 5, on which the coincidence count signal is based for a pixel element 5 arranged at the edge within the matrix of pixel elements 5, is different from the number and/or choice of further pixel elements 5 of the plurality of pixel elements 5, on which the coincidence count signal for a pixel element 5 centrally arranged within the matrix of pixel elements 5 is based. Pixel elements arranged at the edge have, for example, fewer adjacent pixel elements than centrally arranged pixel elements. In addition, different boundary conditions can exist in respect, for example, of the formation of the electrical field in the converter element, and these can be taken into account.

In variant embodiments for a particularly flexible and adjustable implementation of the X-ray detector, the number and/or choice of further pixel elements 5 of the plurality of pixel elements 5 can be designed to be configurable. For example, the number and choice can be designed to be controllable via a control unit and be adaptable thereby. It can also be firmly specified following provision of the photon-counting X-ray detector 1.

According to one advantageously expedient embodiment, the coincidence logic 21 is, in particular in each case, coupled for signaling to at least one comparator 19 of the at least one further pixel element 5 of the plurality of pixel elements 5. The coincidence count signal is then based on the output signals of the comparators 19 of the pixel element 5 being considered, coupled for signaling to the coincidence logic 21 and of the at least one further linked pixel element 5, in this specific case, of the four further pixel elements 5.

The comparators 19 respectively coupled to a coincidence logic 21 can be set to a threshold value, which represents the same energy threshold respectively. For example, the comparator 19 of the pixel element 5 shown here, like the further comparators of the four further pixel elements 5 coupled to the coincidence logic 21, in each case has the same energy threshold, for example 40 keV or 60 keV. In addition, other interconnections for signaling can of course also be provided, with, for example, differently set energy thresholds being linked.

The signal output of the coincidence logic 21 is likewise coupled for signaling to the configurable multiplexer 11. In a second setting of the configurable multiplexer 11 the output signal of the coincidence logic 21, in other words, the coincidence count signal, is output, counted and at least temporarily stored at the counting element 13 instead of the output signal of the comparator 19.

The counting element 13 can then be read out via a control and read-out unit 14. The control and read-out unit 14 can be implemented, for example, also in a peripheral electronic device 65.

In addition, a further signal output 31 linked to the comparator 19 of the illustrated pixel element 5, is provided, which can in turn serve to provide an input signal of a coincidence logic 21 of a second pixel element 5 (not shown here) of the partial number of the plurality of pixel elements 5.

Furthermore, the pixel element 5 (shown here) of the partial number of the plurality of pixel elements 5 can have at least one setting element 23 for runtime adjustment, pulse length adjustment or for delaying an input signal in the at least one coincidence logic 21. In this example, one setting element 23 is indicated for each signal input 29 of the coincidence logic 21 for the runtime adjustment or for delaying the input signals. The setting elements 23 can each be configurable, in other words, settable or controllable, via a control unit 53, so they can optionally also be adjusted following provision of the photon-counting X-ray detector 1. The setting elements 23 can serve to balance signal differences, for example different runtimes due to signal cables of different length, or also to define a time window, within which signals that occur are deemed to be coincident, in other words, are associated with the same photon event.

In variant embodiments, the pixel element 5 of the partial number of the plurality of pixel elements 5 can also comprise at least one electronic element 25 for preventing paralysis of the at least one configurable counter 9. The electronic element 25 can, as indicated here in the schematic representation, be connected for signaling upstream of a respective configurable multiplexer 11. This means that it can in each case be arranged between the signal output of the comparator 19 coupled to the configurable counter 9 and the signal input of the configurable multiplexer 11. The at least one electronic element 25 for preventing paralysis can also be connected for signaling downstream of the configurable multiplexer 11 in each case. This means that it can be arranged between the signal output of the respective configurable multiplexer 11 and the signal input of the respective counting element 13 of the configurable counter 9. Advantageously, improved high flux behavior of the pixel element 5 can be achieved.

The electronic element 25 can be designed, for example, as a pile-up trigger (see for example Kraft et al. "Experimental evaluation of the pile-up trigger method in a revised quantum-counting CT detector", Proc. SPIE 8313, Medical Imaging 2012: Physics of Medical Imaging, 83134A (2012); https://doi.org/10.1117/12.911231, the entire contents of which is hereby incorporated herein by reference) or as what is known as an "instant retrigger" (Loeliger et al. "The new PILATUS3 ASIC with instant retrigger capability", 2012 IEEE Nuclear Science Symposium and Medical Imaging Conference Record (NSS/MIC) (2012); https://doi.org/610-615.10.1109/NSSMIC.2012.6551180, the entire contents of which is hereby incorporated herein by reference).

One pixel element 5 of the partial number of the plurality of pixel elements 5 can, moreover, have even further elements for processing the generated signals which are not illustrated further here. In particular, one pixel element 5 of the partial number of the plurality of pixel elements 5 can have a plurality of comparators 19 each with a settable threshold value THR, which are each coupled for signaling to the signal amplifier 17. In this way a plurality of energy thresholds can be provided. In particular the further comparators 19 can be coupled either to further configurable counters 9 or also to non-configurable, regular counters comprising a counting element 13.

For example, each configurable counter can be rededicated per configuration bit from one counting mode to the other counting mode.

Figure 3:
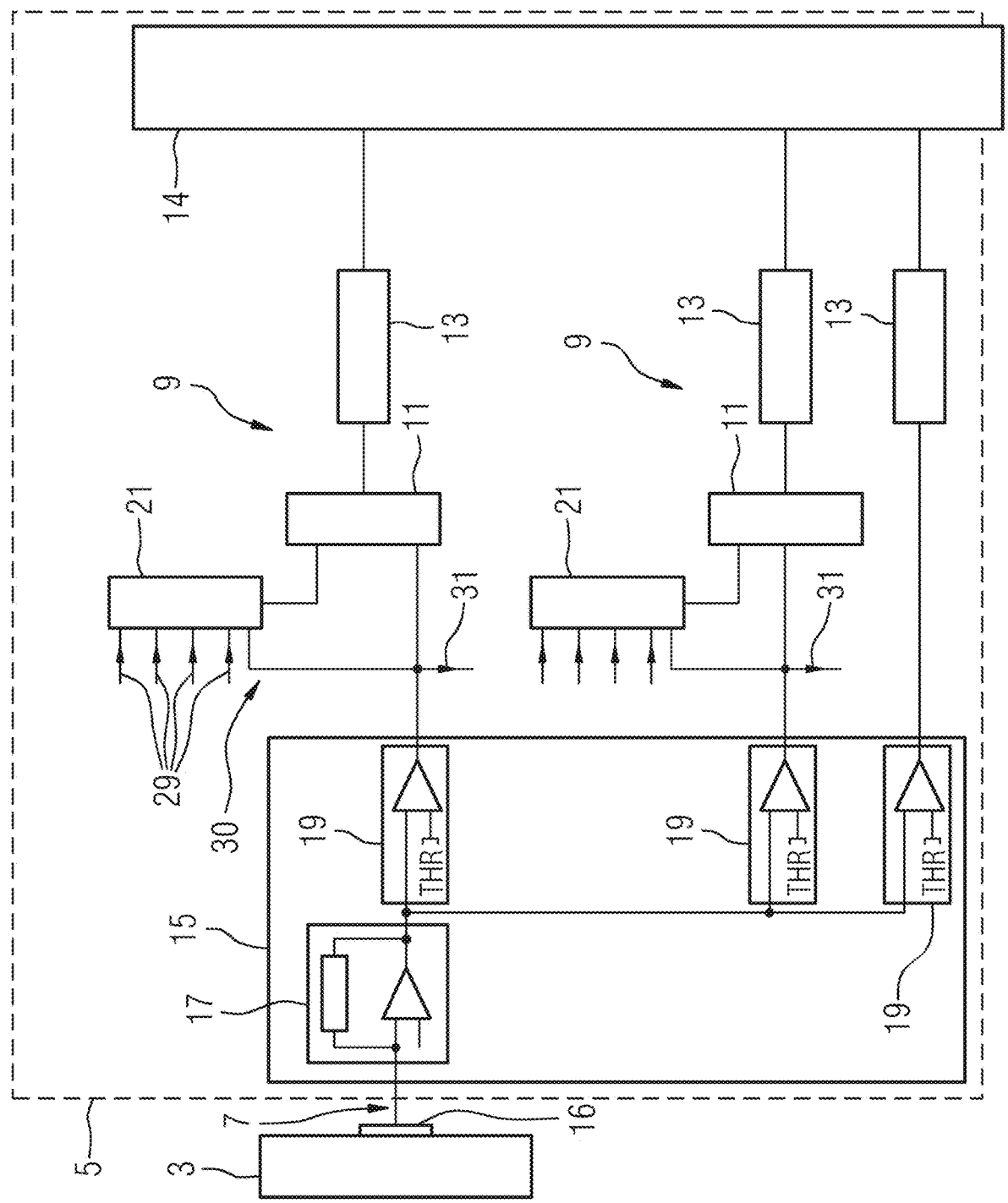
FIG. 3 shows a diagram as an illustration of an interconnection for signaling of a pixel element according to a second variant embodiment.

FIG. 3 shows a diagram as an illustration of interconnection for signaling of a configurable pixel element 5 of the partial number of the plurality of pixel elements 5 of a photon-counting X-ray detector 1 according to a second variant with a configurable counter 9.

Here the pixel element 5 of the partial number of the plurality of pixel elements 5 has a plurality of comparators 19 each with a settable threshold value THR. Two of the comparators 19 are in each case connected for signaling to a configurable counter 9 and in each case to a coincidence logic 21. By contrast, a third comparator 19 is coupled for signaling only to a regular counting element 13. The third comparator 19 is thereby only designed to count pixel count signals based on the output signal of the coupled comparator 19 and as a function of its threshold value THR. Depending on the setting of the respective configurable counter 9, the two other comparators can each count either according to the first setting, pixel count signals based on the signal output of their associated comparator 19 or according to the second setting, coincidence count signals based on the output signals of the respectively coupled coincidence logic 21. In other variants all comparators 19 or just one comparator 19 can also be connected to a configurable counter 9.

Preferably, at least one comparator 19 is coupled to a configurable counter 9. If the remaining comparators are then provided with regular counters, this implementation comprises advantageously low routing complexity and a low power consumption. Advantageously, at least the comparator 19, which is set to the lowest energy threshold value THR, compared to the other comparators 19 of the pixel element, or can be set to the lowest energy threshold value THR, is coupled to a configurable counter 9. Coincidence information as a function of the energy threshold set to the lowest energy already facilitates far-reaching correction possibilities with optimally low complexity. Advantageously, this can be combined with the possibility of setting threshold values THR of at least some of the comparators 19 of a pixel element 5 at least in overlapping energy fields. This makes it possible for the threshold values of two comparators 19 to represent essentially the same energy threshold. In this way coincidence information can be gathered in a pixel element 5 as a function of an energy threshold without having to dispense with pixel count signals as a function of the same energy threshold.

Figure 4:
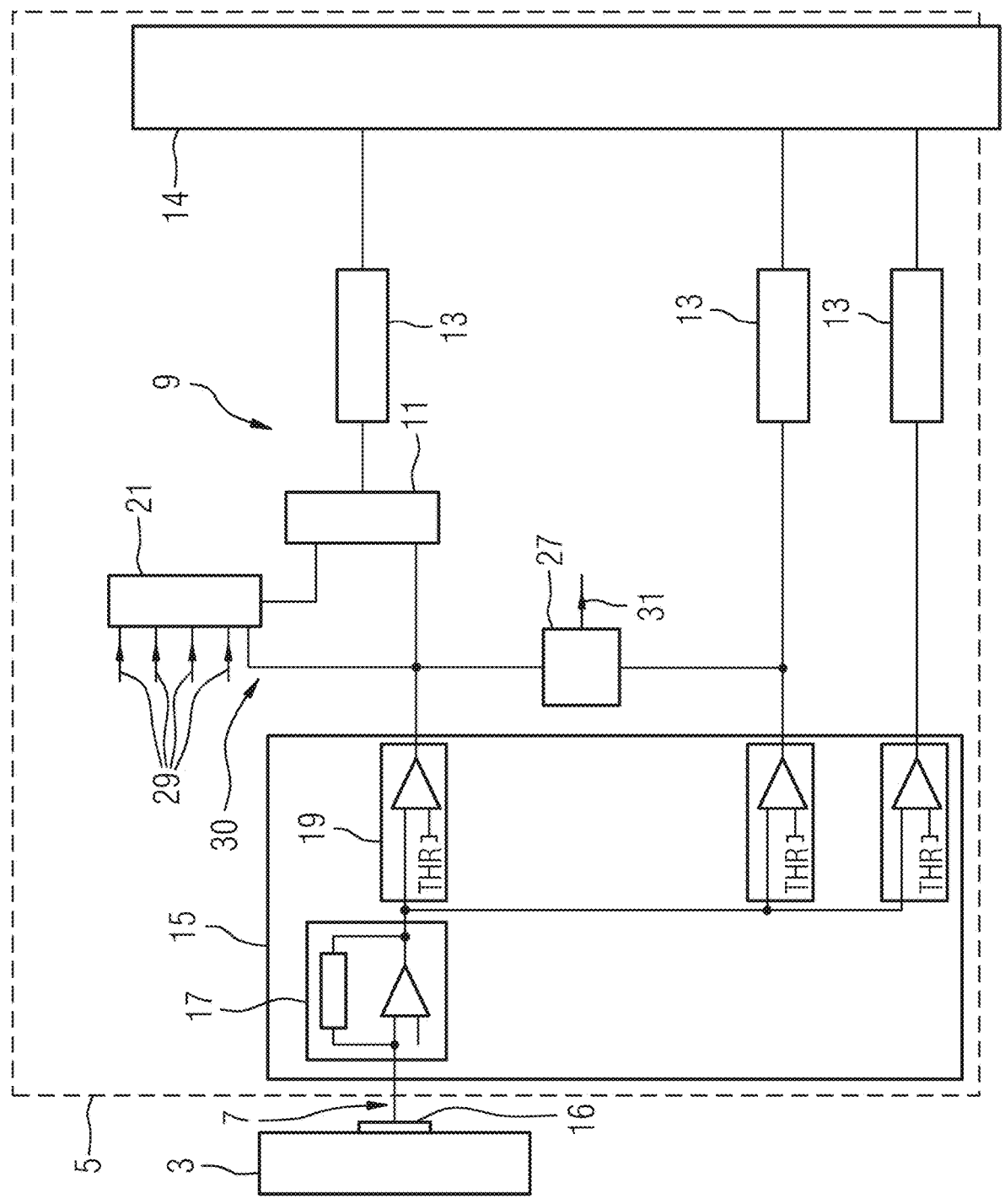
FIG. 4 shows a diagram as an illustration of an interconnection for signaling of a pixel element according to a third variant embodiment.

FIG. 4 shows a diagram as an illustration of an interconnection for signaling of a configurable pixel element 5 of the partial number of the plurality of pixel elements 5 of a photon-counting X-ray detector 1 according to a third variant with a configurable counter 9.

The pixel element 5 (shown here) of the partial number of the plurality of pixel elements 5 has a further switching element 27. The further switching element is linked for signaling to the signal outputs of two of the comparators 19 of the pixel element 5 being considered. The switching element 27, for example also comprising a multiplexer, is designed to either output the output signal of the first comparator 19 or the output signal of the second comparator 19 via the signal output 31 to at least one second pixel element 5 (not shown) of the partial number of the plurality of pixel elements 5. The emitted output signal can then be fed accordingly as an input signal via a signal input 29 into a coincidence logic 21 of a pixel element 5 (not shown here) of the partial number of the plurality of pixel elements 5.

In particular, the at least one coincidence logic 21 of a respective pixel element 5 of the partial number of the plurality of pixel elements 5 is thereby coupled for signaling to more than one comparator 19 of the at least one further pixel element 5 of the plurality of pixel elements 5.

Via the switching element 27 it is possible, in particular, to configure or switch which comparator 19 serves as the input signal of the coincidence logic 21. It is thereby possible, in particular, to set and easily switch based upon which comparator 19 a coincidence count signal is based. Advantageously, further flexibility can be achieved with simultaneous saving of resources.

In particular in the cases where the threshold value THR of the comparators 19 of a pixel element can in each case be set to only a limited energy field and possibly so as not to overlap the energy fields of further comparators, increased flexibility can be achieved hereby for gathering coincidence information as a function of different energy thresholds.

Figure 5:
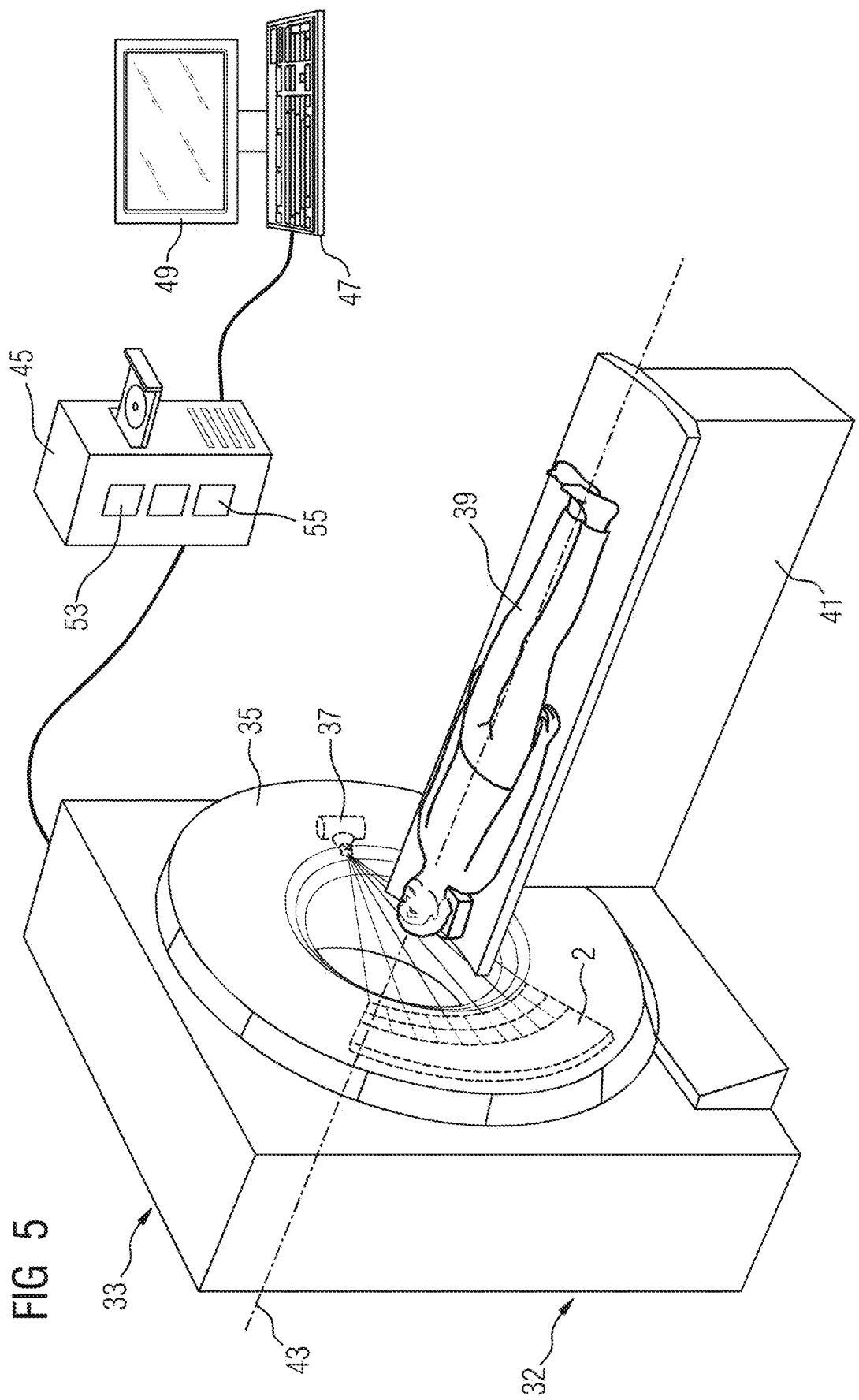
FIG. 5 shows an example medical imaging device.

FIG. 5 shows an example embodiment of an inventive medical imaging device in the form of a computed tomography system 32. The computed tomography system 32 has a gantry 33 with a rotor 35. The rotor 35 comprises a radiation source or X-ray source 37 and a detector 2. The detector 2 has at least one inventive X-ray detector 1. The detector 2 can have a detector module 51 with a number of X-ray detectors 1. The object 39, here the patient, is supported on the patient couch 41 and can be moved along the axis of rotation z 43 through the gantry 33. In general, the object 39 can comprise, for example, an animal patient and/or a human patient. A system controller in the form of an arithmetic unit 45 is provided for controlling the medical imaging device and/or for creating an X-ray image data set based on the counted pixel count signals and/or coincidence count signals.

The arithmetic unit 45 can comprise a control unit 53 for controlling the at least one X-ray detector 1. In particular, the at least one configurable counter 9 of the pixel elements 5 of the partial number of the plurality of pixel elements 5 can be controlled and thereby configured via the control unit 53.

The control unit 53 and/or the arithmetic unit 45 can be implemented in the form of a computer, a microcontroller or an integrated circuit. The control unit 53 and/or the arithmetic unit 45 can have hardware elements or software elements, for example a microprocessor or what is known as an FPGA ("Field Programmable Gate Array"). It can also be a real or virtual group of computers (an English technical term for a real group is "cluster", an English technical term for a virtual group is "cloud", the entire contents of which is hereby incorporated herein by reference).

If configuring of the at least one configurable counter 9 of the pixel elements 5 of the partial number of the plurality of pixel elements 5 is based on one or more parameter(s), for example the parameter(s) can be retrieved for example from a memory 55 or the system controller of the medical imaging device or else be directly determined or measured. Retrieval and/or determination can, in particular, be carried out automatically via the control unit 53.

In the case of a computed tomography system, conventionally a (raw) X-ray image data set of the object is acquired via the X-ray detector from a plurality of angles. A final X-ray image data set can then be reconstructed based upon the (raw) X-ray image data set via a mathematical method, for example comprising a filtered back projection or an iterative reconstruction method.

Depending on the interconnection for signaling of the pixel elements 5 of the plurality of pixel elements 5 and after respective configuration of the configurable counters of the pixel elements 5 of the partial number of the plurality of pixel elements 5, the (raw) X-ray image data set can comprise, (raw) X-ray images based on counted numbers of pixel count signals, counted numbers of coincidence count signals or based on both. The numbers of pixel count signals and the numbers of coincidence count signals or the (raw) X-ray images based thereon can also be present as a function of a plurality of threshold values, in other words, energy thresholds. In particular, counted numbers of coincidence count signals can be used for correction of the counted numbers of pixel count signals, it being possible for an X-ray image data set resulting therefrom to then be based on the corrected numbers. A correction can also be carried out first on the image plane.

Furthermore, an input device 47 and an output device 49 are connected to the arithmetic unit 45. The input device and the output device can enable, for example, an interaction, for example a manual configuration, an acknowledgement or triggering of a method step by a user.

Figure 6:
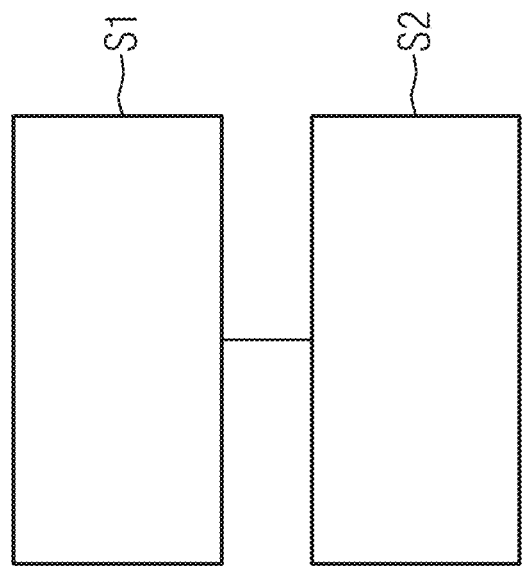
FIG. 6 shows a schematic flow of a method for operating a photon-counting X-ray detector.

FIG. 6 shows a schematic method flow of a method for operating an inventive photon-counting X-ray detector for acquiring an X-ray image data set of an object 39 penetrated by X-ray radiation, wherein in a first counting mode the at least one configurable counter 9 counts a pixel count signal, which is based on a signal that has been received directly in each pixel element 5 of the partial number of the plurality of pixel elements 5 and in a second counting mode of the configurable counter 9 counts a coincidence count signal, which is based on the signal that has been received directly in the respective pixel element 5 and on a coincident signal of at least one further pixel element 5 of the plurality of pixel elements 5, and wherein it is possible to switch between the first and the second counting modes.

Step S1 in FIG. 6 comprises providing the photon-counting X-ray detector 1 in a first configuration of the pixel elements 5 of the partial number of the plurality of pixel elements 5, with the at least one configurable counter 9 of the pixel elements 5 of the partial number of the plurality of pixel elements 5 being configured either for the first or for the second counting mode.

Step S2 in FIG. 6 comprises configuring of the photon-counting X-ray detector 1 from step 1, wherein at least for some of the pixel elements 5 of the partial number of the plurality of pixel elements 5 the counting mode is switched to in that the at least one configurable counter 9 of at least some of the pixel elements 5 of the partial number of the plurality of pixel elements 5 is switched from the first to the second setting.

In this case it can be provided that the at least one configurable counter is individually configured for each pixel element of the partial number of the plurality of pixel elements 5. A configuration in groups of pixel elements 5 of the partial number of the plurality of pixel elements can also be provided. A group can also comprise all of the at least partial number and therewith also all of the plurality of pixel elements.

Configuring can also comprise a choice or number of further pixel elements being individually configured for each pixel element of the partial number of the plurality of pixel elements 5 or on a group basis. Configuring can also comprise that it is configured on which comparators, and therewith threshold values, the coincidence count signal, which is counted via the configurable counter, is based.

A step of retrieval and/or determination of at least one parameter of the medical imaging device, the X-ray detector and/or a respective pixel element can also be provided.

It can be provided that the configuration of the pixel elements 5 of the partial number of the plurality of pixel elements 5 is dependent on one or more parameter(s). The parameter(s) can be retrieved, for example, from a memory or a system controller of the X-ray system or else be determined directly, for example measured via the X-ray detector. The at least one parameter can be based, for example, on an X-ray flow. A controller can also be provided, for example dependent on the count rate (dose/unit of time) expected for the application. The parameter can also comprise a position of a pixel element. The parameter can also be determined in another way.

The step of configuring S2 can be carried out in particular automatically via a control unit 53 in that the configurable counter is automatically controlled and configured. Manual activation can also be provided if required. Automatic control can occur in conjunction with the determined parameter(s).

Automatic implementation of a step of retrieval and/or determination via a control unit 53 can also be provided.

Furthermore, the method can comprise pixel-by-pixel conversion of the X-ray radiation penetrating the object and impinging the X-ray detector into electrical signals in the pixel elements. Furthermore, the method can comprise a conversion of the electrical signals into pixel count signals and/or into coincidence count signals, depending on the configuration and interconnection, and storage of the counted numbers in the pixel elements. Reading out of the counted numbers of pixel count signals and/or coincidence count signals and creation of one or more image data set(s) representing the object can then be provided.

According to one variant embodiment of the method, for the case where both pixel count signals and coincidence count signals are counted, the numbers of coincidence count signals or X-ray images, which are based on the numbers of coincidence count signals, can be used for correction of the numbers of pixel count signals or X-ray images, which are based on the numbers of pixel count signals.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A photon-counting X-ray detector for acquiring an X-ray image data set of an object penetrated by X-ray radiation, the photon-counting X-ray detector comprising:
   a converter element, configured to convert incident X-ray radiation into an electrical signal; and
   a matrix of a plurality of pixel elements, at least a partial number of the plurality of pixel elements configured to receive a signal input based on the electrical signal; and
   at least one configurable counter coupled to the at least a partial number of the plurality of pixel elements, the at least one configurable counter including a configurable multiplexer configured to cause the at least one configurable counter to
       count a pixel count in response to the configurable multiplexer being set to a first setting, the pixel count based on a direct signal received in a respective pixel element of the partial number of the plurality of pixel elements, and
       count a coincidence count in response to the configurable multiplexer being set to a second setting, the coincidence count based on the direct signal received in the respective pixel element and on a coincident signal of at least one further pixel element of the plurality of pixel elements.

2. The photon-counting X-ray detector of claim 1, wherein the at least one configurable counter is at least one of
   individually configurable for each respective pixel element of the partial number of the plurality of pixel elements, or
   jointly configurable for a group of pixel elements of the partial number of the plurality of pixel elements.

3. The photon-counting X-ray detector of claim 2, wherein each respective pixel element of the plurality of pixel elements includes a conversion apparatus connected to a respective signal input, each conversion apparatus including at least one signal amplifier and a number of comparators, and each comparator of the number of comparators respectively having a settable threshold value, and
   wherein for each respective pixel element of the partial number of the plurality of pixel elements, at least one comparator of the number of comparators is coupled to the at least one configurable counter.

4. The photon-counting X-ray detector of claim 3, wherein each respective pixel element of the partial number of the plurality of pixel elements includes at least one coincidence logic coupled to at least one comparator of the respective pixel element and to at least one comparator of the at least one further pixel element, and
   wherein the coincidence count is based on an output signal of the coincidence logic.

5. The photon-counting X-ray detector of claim 4, wherein each respective pixel element of the plurality of pixel elements includes a plurality of comparators, and
   wherein the at least one coincidence logic of a pixel element of the partial number of the plurality of pixel elements is coupled to more than one comparator of the at least one further pixel element of the plurality of pixel elements.

6. The photon-counting X-ray detector of claim 1, wherein each respective pixel element of the plurality of pixel elements includes a conversion apparatus connected to a respective signal input, each conversion apparatus including at least one signal amplifier and a number of comparators, and each comparator of the number of comparators respectively having a settable threshold value, and
   wherein for each respective pixel element of the partial number of the plurality of pixel elements, at least one comparator of the number of comparators is coupled to the at least one configurable counter.

7. The photon-counting X-ray detector of claim 6, wherein each respective pixel element of the partial number of the plurality of pixel elements includes at least one coincidence logic coupled to at least one comparator of the respective pixel element and to at least one comparator of the at least one further pixel element, and
wherein the coincidence count is based on an output signal of the coincidence logic.

8. The photon-counting X-ray detector of claim 7, wherein each respective pixel element of the plurality of pixel elements includes a plurality of comparators, and
wherein the at least one coincidence logic of a pixel element of the partial number of the plurality of pixel elements is coupled to more than one comparator of the at least one further pixel element of the plurality of pixel elements.

9. The photon-counting X-ray detector of claim 7, wherein each respective pixel element of the partial number of the plurality of pixel elements includes at least one setting element configurable for at least one of runtime adjustment, or delaying an input signal into the at least one coincidence logic.

10. The photon-counting X-ray detector of claim 6, wherein each respective pixel element of the partial number of the plurality of pixel elements includes a plurality of configurable counters, each configurable counter of the plurality of configurable counters respectively coupled to at least one comparator of the respective pixel element and to at least one comparator of the at least one further pixel element of the plurality of pixel elements.

11. The photon-counting X-ray detector of claim 6, wherein the at least one configurable counter is at least one of
individually configurable for each respective pixel element of the partial number of the plurality of pixel elements, or
jointly configurable for a group of pixel elements of the partial number of the plurality of pixel elements.

12. The photon-counting X-ray detector of claim 1, wherein the coincidence count signal is based on
the direct signal received in the respective pixel element of the partial number of the plurality of pixel elements, and
coincident signals of between one and 24 further pixel elements of the plurality of pixel elements.

13. The photon-counting X-ray detector of claim 1, wherein at least one of a number or a choice of further pixel elements of the plurality of pixel elements, on which the coincidence count signal is based, is different for different pixel elements of the plurality of pixel elements.

14. The photon-counting X-ray detector of claim 1, wherein at least one of a number or choice of further pixel elements of the plurality of pixel elements, on which the coincidence count signal for a pixel element arranged at an edge within the matrix of pixel elements is based, is different from at least one of a number or choice of further pixel elements of the plurality of pixel elements, on which the coincidence count signal for a pixel element arranged centrally within the matrix of pixel elements is based.

15. The photon-counting X-ray detector of claim 1, wherein each respective pixel element of the partial number of the plurality of pixel elements includes at least one electronic element configured to prevent paralysis of the at least one configurable counter.

16. A medical imaging device, comprising:
the photon-counting X-ray detector of claim 1.

17. The medical imaging device of claim 16, wherein the medical imaging device is a computed tomography system.

18. A method for operating a photon-counting X-ray detector for acquiring an X-ray image data set of an object penetrated by X-ray radiation, the method comprising:
counting a pixel count, in response to a configurable multiplexer of at least one configurable counter of a respective pixel element of a partial number of a plurality of pixel elements of the photon-counting X-ray detector being set to a first counting mode, the pixel count signal based on a direct signal received in the respective pixel element of the partial number of the plurality of pixel elements; and
counting a coincidence count, in response to the configurable multiplexer being set to a second counting mode, the coincidence count based on the direct signal received in the respective pixel element and on a coincident signal of at least one further pixel element of the plurality of pixel elements,
wherein the at least one configurable counter is configured to be switchable between the first counting mode and the second counting mode.

19. The method of claim 18, wherein the at least one configurable counter is at least one of
individually configurable for each respective pixel element of the partial number of the plurality of pixel elements, or
jointly configurable for a group of pixel elements of the partial number of the plurality of pixel elements.

* * * * *